United States Patent [19]
Summer

[11] Patent Number: 6,142,778
[45] Date of Patent: *Nov. 7, 2000

[54] DENTAL INSERT

[76] Inventor: John D. Summer, 9601 NW. Leahy Rd., #305, Portland, Oreg. 97229

[ * ] Notice: This patent issued on a continued prosecution application filed under 37 CFR 1.53(d), and is subject to the twenty year patent term provisions of 35 U.S.C. 154(a)(2).

[21] Appl. No.: 09/358,684

[22] Filed: Jul. 21, 1999

[51] Int. Cl.[7] .................................................. A61C 5/04
[52] U.S. Cl. ............................................................ 433/39
[58] Field of Search ............................. 433/39, 158, 40, 433/149

[56] References Cited

U.S. PATENT DOCUMENTS

| | | | |
|---|---|---|---|
| 2,607,117 | 8/1952 | Baughan | 433/39 |
| 3,145,472 | 8/1964 | Tofflemire | 433/39 |
| 3,305,928 | 2/1967 | Tofflemire | 433/39 |
| 5,342,194 | 8/1994 | Feldman | 433/39 |
| 5,380,198 | 1/1995 | Suhonen | 433/39 |

*Primary Examiner*—Todd E. Manahan
*Attorney, Agent, or Firm*—Klarquist Sparkman Campbell Leigh & Whinston LLP

[57] ABSTRACT

Tooth inserts are described for positioning between interproximal surfaces of teeth during a dental procedure. The tooth inserts have thin regions positioned in the interproximal contact area of the teeth.

19 Claims, 4 Drawing Sheets

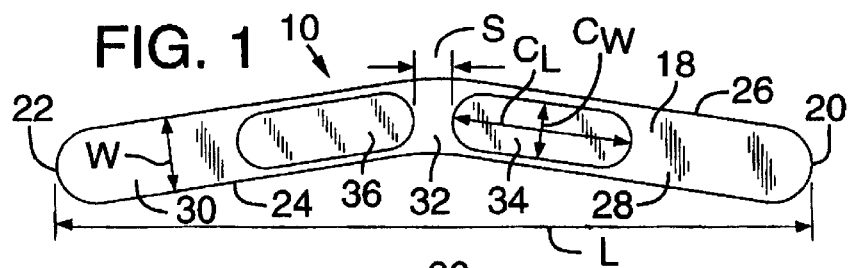
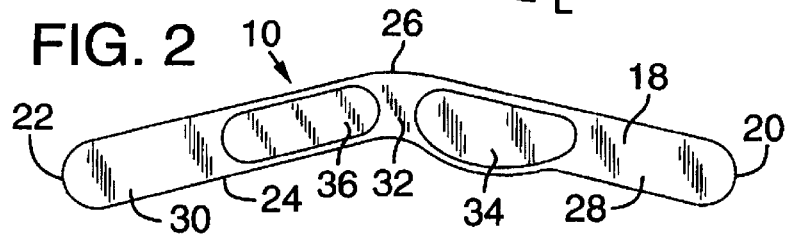
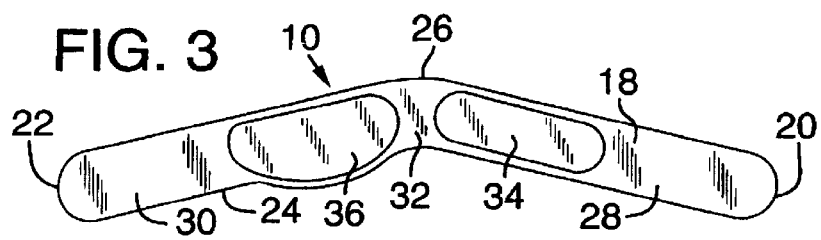
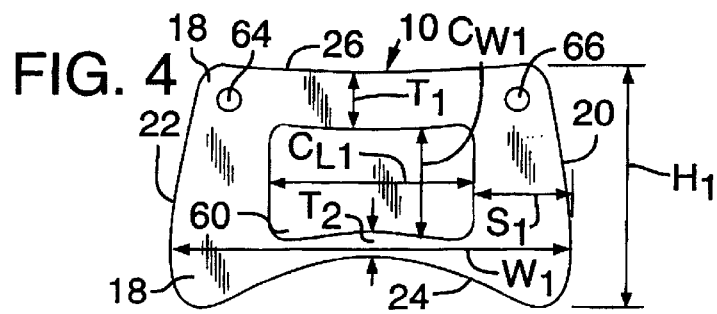
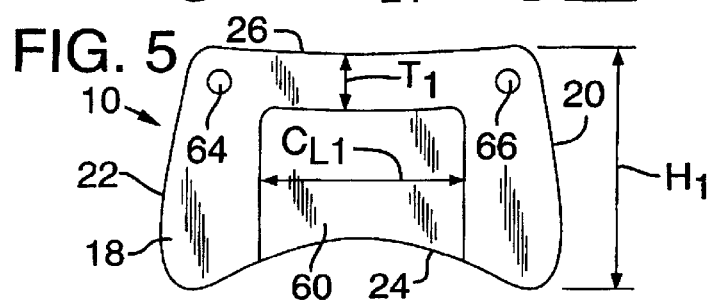
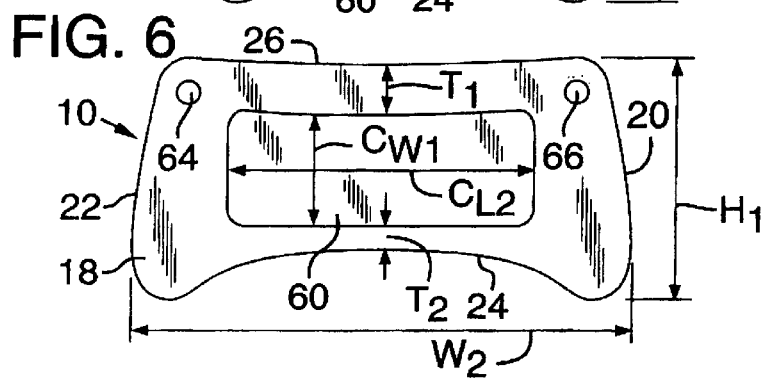

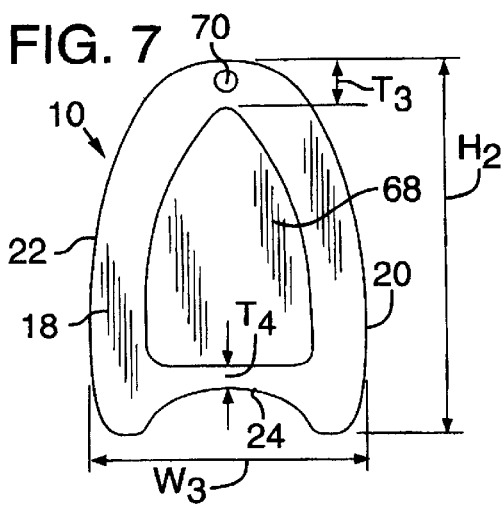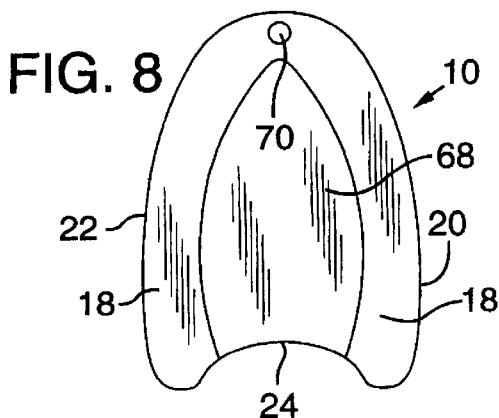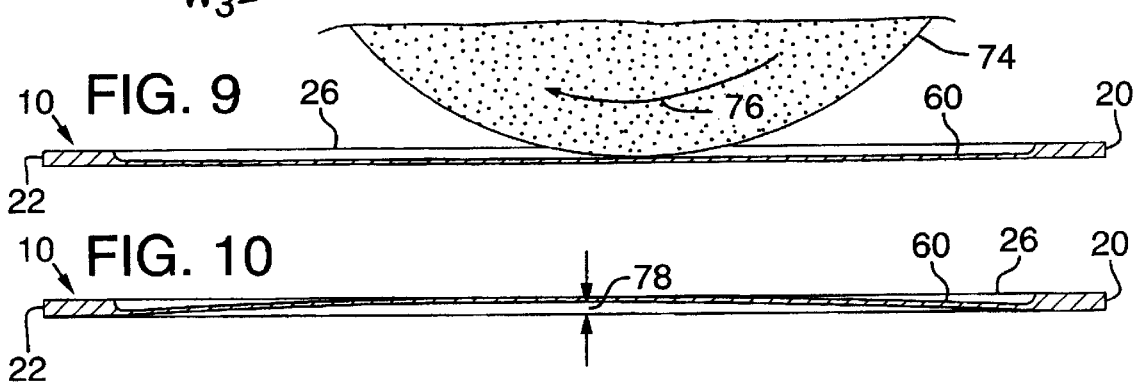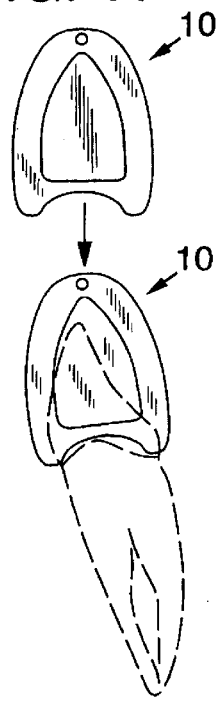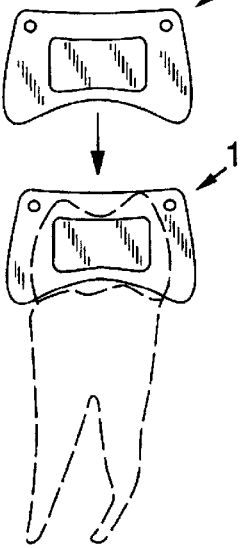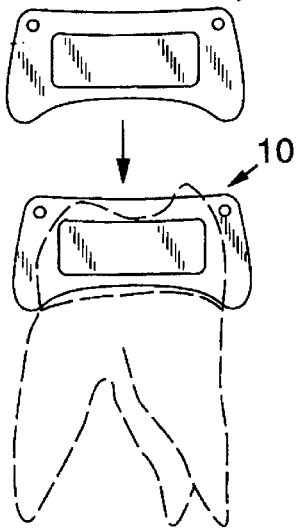

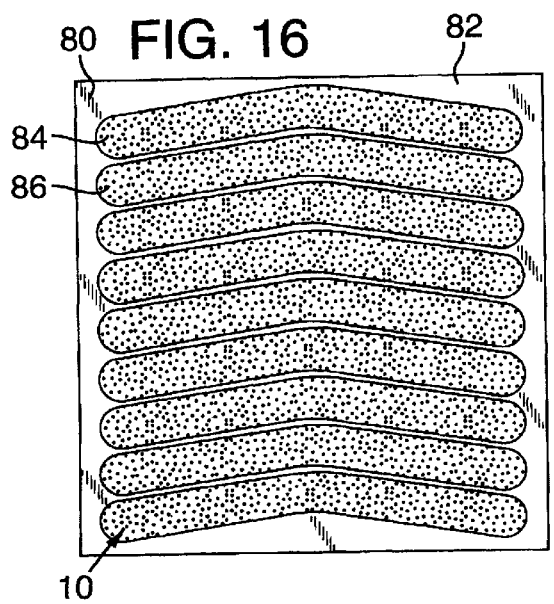
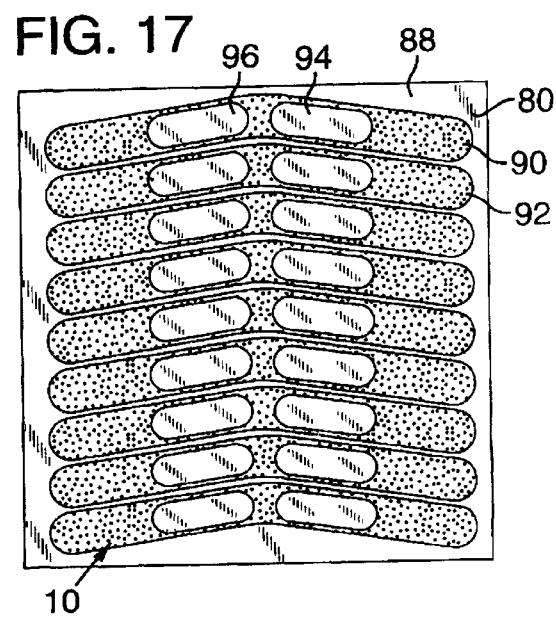
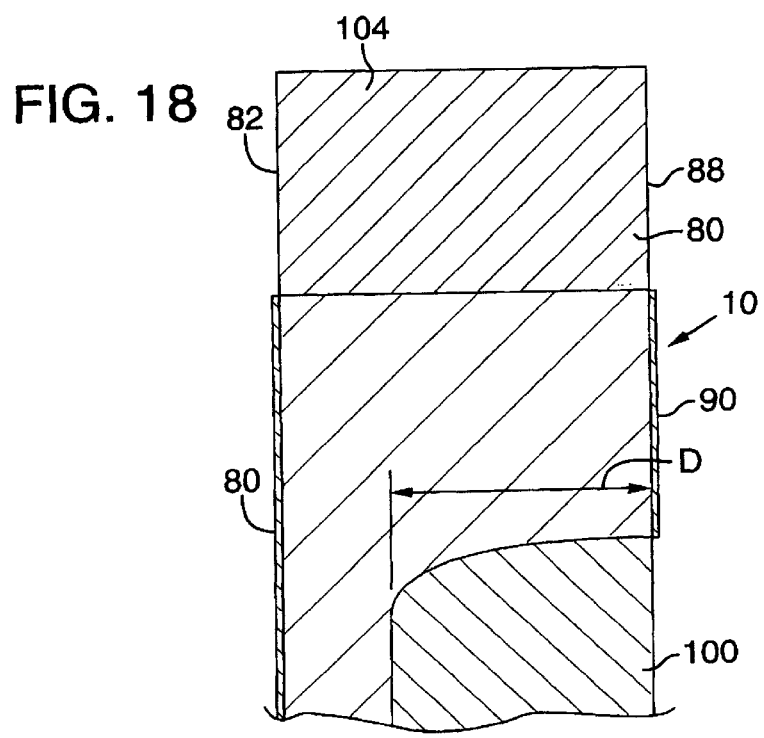

DENTAL INSERT

The present invention relates to the field of dental devices and particularly to tooth inserts for positioning between teeth.

A class 2 filling is a dental procedure in which a decayed area of a tooth along a portion of a proximal surface, that is a part of the tooth which contacts an adjacent tooth, is prepared and filled. In restoring the proximal surface of the tooth being treated in connection with such a filling, it is important to recreate a tight contact with the adjacent teeth. A proximal contact which is even 0.001 inch open may allow food impaction and result in recurrent decay.

For decades dentists have used silver amalgam as a filling material for class 2 fillings. Silver amalgam is very dense and is also compactible. As a result, packing this type of material forcefully into the part of the cavity preparation known as the proximal box drives apart the tooth being filled and its adjacent tooth by, for example, about 0.0015 inch during the procedure. During this procedure, a matrix band surrounds the tooth which is being treated. Following the completion of the filling and the removal of the matrix band, the adjacent tooth and the tooth being filled spring back together about 0.0015 inch, resulting in a fully closed contact between the restored proximal surface and the adjacent tooth.

Recently there has been a movement toward using composite resins rather than silver amalgam for fillings, in part because of possible dangers from mercury in amalgam and also because of the tooth-like color achievable in composite resins. However, composite resins in general are not nearly as dense or compactable as silver amalgam. Consequently, these resins are difficult to pack into the proximal box of a class two filling sufficiently to drive apart the tooth receiving the filling and the adjacent tooth (or teeth in the case where proximal surfaces at both sides of the tooth are being treated). Consequently, when a commonly used matrix band is removed from a class 2 filling made with composite material, a gap often remains between the filled tooth and the adjacent tooth. The gap is typically roughly as wide as the thickness of the matrix band which was used in the filling. For example, about 0.001 to 0.0015 inch wide for many types of matrix bands. These gaps are too wide to allow creation of a good proximal contact.

One recent attempt to solve the problem of open contacts in class 2 composite fillings has been to use so-called "condensable" composite resins formulated to be as much as possible like silver amalgam in their handling properties and their ability to be condensed or compacted when packed tightly into a hole or void in a tooth. However, problems still remain as resins of this type known to the inventor at this time are not dense enough or compactable enough to entirely solve the open contact problem.

Doctors sometimes employ special techniques and tools to wedge apart or otherwise force apart the adjacent teeth during the filling process so that the teeth then spring back to provide the desired post-contact following the dental procedure. That is, systems have been employed to forcefully separate adjacent teeth during the filling process, much like the separation produced by packing dental amalgam into a proximal box. For example, mechanical wedges driven in place by finger pressure between adjacent teeth at a location well below the contact area have been used. U.S. Pat. No. 5,791,898, discloses an approach in which teeth are forcefully separated and then stabilized using a light curing tip. Another known technique involves forcefully separating the teeth by use of a metal ring (called bitine ring) which applies powerful forces inward between the teeth at a location just beneath where they meet. Such rings have been available from Palodent, a division of Darway, Inc. of San Mateo, Calif. and also from Garrison Dental Solutions of Spring Lake, Mich.

U.S. Pat. No. 5,505,618 to Summer discloses a tooth spacer for insertion between the proximal surfaces of teeth. The tooth spacer has a body with a thin central portion partially surrounded by or enclosed by a peripheral re-enforcing portion. Various ways of forming a tooth spacer, including chemical etching, are disclosed in the Summer patent. The reinforcing portion may range from about 0.0015 to 0.003 inch, although it may be thicker. The thin central portion preferably has a thickness ranging from 0.0001 to 0.001 inch. As a result, tooth spacers of this patent may be positioned between the interproximal surfaces between adjacent teeth while virtually eliminating any wedging of the teeth apart. The patent U.S. Pat. No. 5,505,618 is incorporated by reference therein in it entirety.

A need nevertheless remains for improved tooth inserts.

SUMMARY

In one form, a tooth insert comprises an elongated band having spaced apart thin central regions positioned so that, when the band is wrapped around a tooth, a first of the central regions is positioned between a first tooth and an adjacent second tooth and the second of the second of the central regions is positioned between the first tooth and a third tooth which is adjacent to the first tooth and at the opposite side of the first tooth from the second tooth. Thus, the thin central regions are positioned between the interproximal surfaces of the first tooth and the second and third teeth on the respective sides of the first tooth. The body may include a reinforcing region extending partially or entirely around the thin central regions. That is, the thin central regions may extend entirely to the gingival edge of the body or may be spaced from the gingival edge by a reinforcing portion of the body. A reinforcing portion of the body is typically also positioned between the spaced apart thin central regions. One or both of the central regions may be enlarged in a direction toward the gingival edge of the body for use, for example, in cases where a deep filling is being completed. The thin interproximal contact areas or central regions typically range in thickness from about 0.0001 inch to somewhat less than 0.001 inch, with 0.0003 inch to 0.0007 inch being a preferred range and with a specific example being about 0.0045 inch thick. The reinforcing region may vary in thickness with an exemplary range being from about 0.0015 inch to 0.003 inch, although it may be thicker. The superstructure or reinforcing portion of the insert maintains the overall rigidity of the insert and facilitates insertion of the insert or band between adjacent teeth on both sides of a tooth which has been prepared for treatment, for example, for a class 2 filling.

The thin central regions may bulge in one direction prior to use of the insert to form a generally concave area. The concave area may be positioned adjacent to the tooth which is to be filled when the tooth insert is placed in position. It has been found that polishing or buffing the thin area following its formation causes the thin area to be drawn toward the buffing wheel resulting in the concavity or bulge.

Teeth inserts of various forms are also shown with one such insert being of a generally triangular configuration with arcuate sides and an arcuate bottom or gingival edge. The central thin region may extend entirely to the gingival edge or may be spaced from the gingival edge with the reinforcing material being positioned along the sides of the insert. In other forms, the inserts may assume a generally trapezoidal shape with an arcuate gingival edge, again with the thin central region extending to the gingival edge or being spaced from the gingival edge. A concavity or bulged area may also be established in these inserts.

The present invention is defined by the claims below and is directed toward novel and unobvious elements and steps, individually as well as in combination with one another.

BRIEF DESCRIPTION OF THE DRAWINGS

FIG. 1 shows a side view of one embodiment of an elongated band having first and second thin central regions surrounded by a reinforcing body portion of the band.

FIGS. 2 and 3 show side views of a band similar to FIG. 1 each with a respective one of the central regions being enlarged in a direction toward the gingival edge of the band relative to the other central region, it being understood that both of the thin central regions may be enlarged in this manner.

FIGS. 4 through 8 are side views of embodiments of tooth inserts in accordance with the present invention.

FIGS. 9 and 10 illustrate one method of forming a concavity or bulge in the thin central region of tooth inserts, such as of the types shown in FIGS. 1–8.

FIGS. 11 and 13 schematically illustrate the positioning of inserts of FIGS. 7, 4 and 6 in position relative to respective teeth.

FIGS. 16–18 illustrate one approach for manufacturing tooth inserts of the form of FIG. 1, it being understood that this approach may be used in connection with manufacturing tooth inserts of other forms.

DETAILED DESCRIPTION

Figure 14:
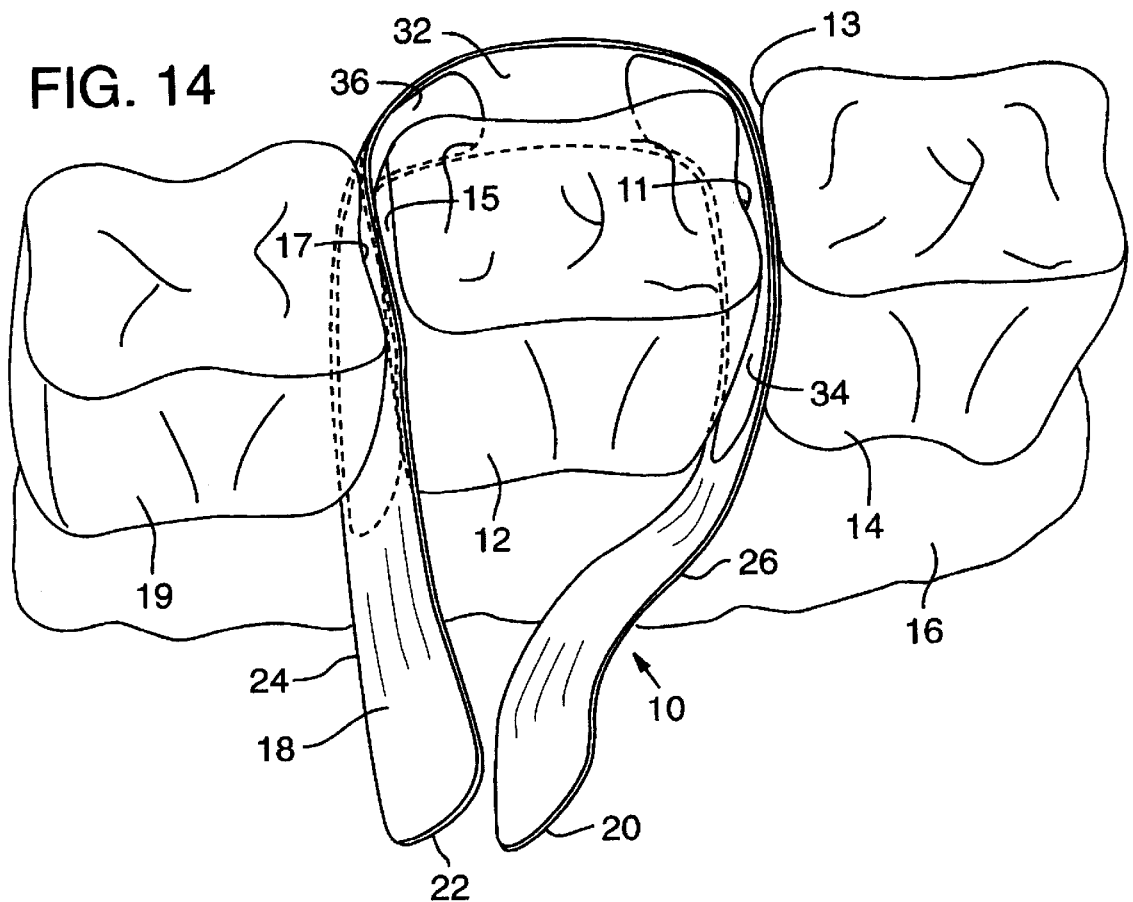
FIG. 14 illustrates the use of a tooth insert of the form shown in FIG. 1.

FIGS. 1–3 illustrate several embodiments of a tooth insert 10. As best seen in FIG. 14, the tooth insert 10 may be inserted between the interproximal surfaces 11, 13 respectively of a tooth 12 to be treated and an adjacent tooth 14. As shown in FIG. 14, the tooth insert of FIG. 1 is sufficiently elongated and long enough to wrap at least partially around the tooth 12 so that the illustrated insert may also be positioned between the interproximal surfaces 15, 17 respectively, of the tooth 12 and of a tooth 19. The teeth 14, 19 are thus on opposite sides of the tooth 12, yet each of the teeth 14, 19 is adjacent to a respective proximal surface of the tooth 12. The illustrated teeth 12, 14 and 19 each have a root extending into the gum 16 of a patient's jaw.

The tooth insert 10 may be of any shape, but in FIGS. 1–3 comprises an elongated body 18 having a pair of opposite transversely space side walls or edges 20, 22, a gingival edge 24 and an occlusal edge 26. The term "gingival edge" refers to the edge of the body which is positioned closest to the patient's gum when the insert is inserted in place. The elongated bodies 18 in FIGS. 1, 2 and 3 have a conventional outline shape. In the form shown in these figures, the body 18 includes first and second leg portions 28, 30 which join together at a central region 32 of the insert 10. The body 18 in these figures is of a somewhat inverted v-shaped configuration with the apex of the configuration being positioned at the central region 32. The elongated body 18 of the FIGS. 1–3 embodiments include at least one and most preferably two recessed or thin central portions 34, 36 each positioned in a respective one of the legs 28, 30. In addition, as can be seen in FIG. 14, the central regions 34, 36 are located on the body 18 so that these central regions are positioned in the interproximal contact areas between the adjacent teeth. Thus, central region 34 is positioned between surfaces 11 and 13 of teeth 12 and 14 while central region 36 is positioned between the contact surfaces 15 and 17 of the teeth 12 and 19. The central regions 34, 36 may extend entirely to the gingival edge 24 of the body. Alternatively, as shown, the central portion may be spaced from the gingival edge. Thus, the central regions 34, 36 are at least partially surrounded or entirely enclosed by a peripheral portion of the body for reinforcing purposes as explained below. The body 18 is preferably of a monolithic or unitary construction and is most preferably, but not necessarily, made of a durable material such as stainless steel. The body may be made of a multiple piece construction and may also be made of other materials.

Although the size of the bands may vary, in one specific example, the overall length L of the body 18 of FIG. 1 from edge 20 to edge 22 is approximately 2.5 inches. In addition, the width of the body 18 in FIG. 1, indicated by W in this figure, measured along a line perpendicular to the respective edges 24, 26, may be 0.25 inch. The spacing between two vertical lines intersecting the adjacent edges of the thin areas 34, 36, indicated by S in FIG. 1, may be about 0.13 inch (0.1264 in being a specific example). In addition, the length of the central regions, such as indicated at $C_L$ for region 34 in FIG. 1, may be about 0.6 inch and the width of the central regions, such as indicated at $C_W$ for region 34 may be about 0.19 inch. These dimensions may be varied. Although other configurations may be used, the illustrated central regions 34, 36 are of a generally oval shape with parallel top and bottom edges. The thickness of the peripheral or the reinforcing position of the body 18 bounding the respective central areas may be varied, with the a range of from about 0.0015 inch to about 0.003 inch being an exemplary range, although the reinforcing portion may be thinner or thicker. A specific example is a thickness of 0.015 inch. Although not necessary, the thickness of the reinforcing region may be uniform. As a result, the tooth insert is flexible so that it may be bent to conform to the tooth shape during insertion. For a stainless steel tooth insert with a reinforcing portion of 0.0015 inch thickness, although variable, a reinforcing occlusal edge have a width of about 0.03 inch is provided between the top edge of the recessed central portions 34, 36 and the adjacent occlusal edge to strengthen the tooth insert in this region. A reinforcing portion of a similar width may be provided along the gingival edge. With other materials or thicker reinforcing portions, the width of the reinforcing portion may be varied. Functionally, the reinforcing portion needs to be strong enough to inhibit the recessed or thin portion of the tooth insert from tearing during insertion between teeth and to provide sufficient rigidity to facilitate the insertion of the tooth insert, e.g., by pushing down on the occlusal edge of the insert as it is inserted. Also, conventional band insertion tools may be used to grip the side edges of the insert for use during insertion of the band into position.

As previously mentioned, the central regions 34, 36 preferably have a thickness ranging from about 0.0001 inch to no more than 0.001 inch. A specific preferred range is from about 0.0003 inch to about 0.0007 inch with a 0.00045 inch thickness following polishing as explained below, being a more specific example. As a result, the band or insert may be positioned between the interproximal surfaces of adjacent teeth while virtually eliminating any wedging of the teeth apart. The thin central portions 34, 36 of the band of FIGS. 1 through 3 as well as the other tooth inserts described below are preferably dimensioned to be larger than the contact area between the adjacent teeth. The central portions 34, 36 may extend all the way to the gingival edge of the band, or terminate short of the gingival edge. Most preferably, the thicker reinforcing portion of the tooth insert is provided as described above and bounds the central portion at least along the sides and top thereof. The reinforcing portion has a thickness greater than the thickness of the central portion to provide reinforcement and rigidity to the tooth insert. The illustrated peripheral or reinforcing portion also extends between the first and second central thin regions 34, 36, along the occlusal edge of the band and at the respective side walls or edges along the sides of the thin central regions. As is also shown, the reinforcing portion may also be positioned along the gingival edge of the tooth spacer as this edge ends up in the gap below the contacting areas of the teeth after the tooth spacer has been inserted.

FIG. 1 illustrates first and second thin central areas 34, 36 which are symmetrical. However, the central areas may also be asymmetrical. As shown in FIGS. 2 and 3, one of the central areas has been enlarged in the direction 20 toward the gingival edge of the body 18. In this case, the enlarged central area extends apically (toward the apex of the root of the tooth) on one side for use with a cavity preparation which extends in this direction. Alternatively, the body may be thinned in only one of the contact areas 34, 36, leaving the other as a monolithic part of the body. Both of the regions 34, 36 may also be enlarged in the gingival direction if desired.

The tooth inserts of FIGS. 4 through 6 each have a single central thinned region 60 formed in a body 18. The shape of the body 18 in these examples is generally trapezoidal with an upper occlusal edges 26 and an upwardly curved arcuate gingival edge 24. The side edges 20, 22 of these inserts are also curved and diverge from one another moving from the occlusal edge toward the gingival edge except toward the bottom of the insert where these side edges again converge to form a curved intersection between the gingival edge and the respective side edges. As shown in these figures, the central thin regions 60 may be spaced from or extend entirely to the gingival edge 24. Optional openings 64, 66 may extend through the reinforced portion of the insert adjacent to the occlusal edge 26, in this case above the respective sides of the insert. Openings 64, 66 may receive a dental implement, such as a pick, for use in removing the inserts after the dental procedure is complete. The thickness of the reinforcing regions and central regions of the FIGS. 1–8 examples may be as described above in connection with the FIGS. 1–3 examples.

Although variable, the width $T_1$ of the reinforced occlusal region may range, for example, between about 0.06 inch to about 0.07 inch although this width may be varied. In addition, the width of the reinforced side regions (one such width being indicated at $S_1$ in the FIG. 4 embodiment) may vary with about 0.012 inch being a specific example. Where a reinforced gingival border is included, a width $T_2$ of about 0.03 inch is a specific example. Thus, a gingival border of about twice the width of the reinforced occlusal border is included in this example when apertures 64, 66 are used. The FIGS. 4 through 6 forms of inserts may have a similar height with a height of about 0.03 inch being a specific example. The overall width $W_1$ of the FIGS. 4 and 5 inserts, as a specific example, may be about 0.5 inch. In contrast, the FIG. 6 insert has an overall width $W_2$, for example, of about 0.62 inch. The height, $C_{W1}$ of thin central region 60 of the insert of FIGS. 4 and 6 may be about 0.19 inch. In addition, the width of the thin central region 60 of the FIGS. 4 and 5 inserts indicated at $C_{L1}$ may be about 0.26 inch. In contrast, the width $C_{L2}$ of the insert of FIG. 6 may be about 0.38 inch. The above dimensions may be varied and are provided as specific examples. Although not shown in FIGS. 4 through 6, the backside of these inserts may be planar. However, the thinned central regions 60 may be bulged or curved (e.g. out of the surface of the sheet in FIGS. 4 through 6), such as when processed in the manner explained in connection with FIGS. 9 and 10 below.

The insert 10 of the form shown in FIGS. 7 and 8 is of a generally triangular configuration with first and second convex curved side edges 20, 22 which are joined together at the apex of the insert. In addition, the inserts of FIGS. 7 and 8 include an arcuate upwardly curved gingival edge 24. In the FIG. 7 form of insert, a thin central region 68 is spaced from the gingival edge as well as from the other edges of the insert by a reinforcing portion of the body 18. In the FIG. 8 form of insert, the thin central region 68 extends to the gingival edge 24. Although the dimensions may vary, as a specific example, the overall width $W_3$ of the inserts of FIGS. 7 and 8 may be about 0.37 inch with the overall height $H_2$ being about 0.5 inch. In addition, the width $T_3$ of the reinforcing region along the top and sides of these inserts may be about 0.6 inch. In the case where the reinforcing portion of the body is positioned along the gingival edge, the width $T_4$ (see FIG. 7) may, for example, be about 0.03 inch. Thus, in this example, $T_4$ is about half the dimension of $T_3$. An optional aperture 70 is provided along the apex of the inserts of FIGS. 7 and 8 for use, for example, to allow a dentist to insert a pick or other dental tool for catching and removing the insert. As in the case of the FIGS. 4 through 6 inserts, the back surfaces of the inserts of the FIGS. 7 and 8 form may be planar. Again, however, if processed for example in accordance with the process of FIGS. 9 and 10 below, the thin portion 68 of the inserts FIG. 7 and 8 may assume an arcuate or concave configuration.

Figure 15:
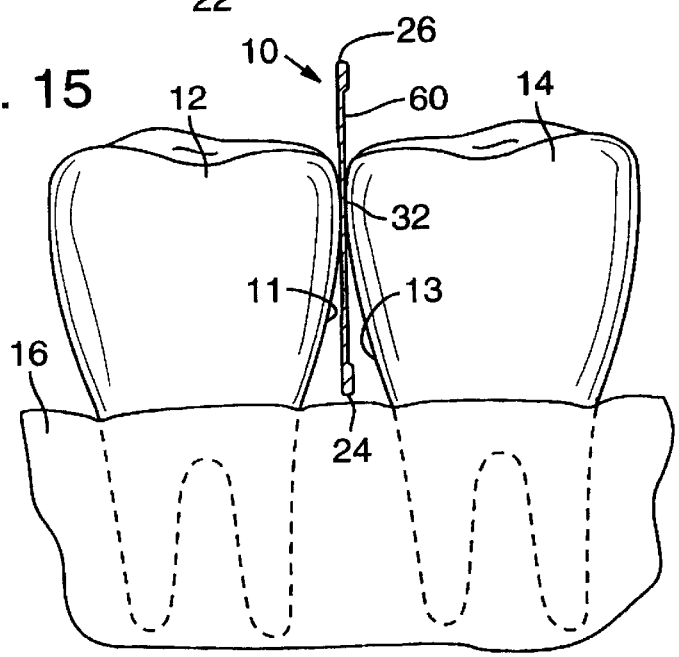
FIG. 15 illustrates the use of a tooth insert of the form shown in FIG. 4.

FIG. 15 illustrates the positioning of an insert of the FIG. 4 form between the teeth 12 and 14.

With reference to FIGS. 9 and 10, following the formation of any of the inserts of FIGS. 1–8 as described above, the central region may be polished or buffed. As a specific example, this procedure is described with reference to the insert of the form shown in FIG. 6. More specifically, a polishing wheel or grinder indicated at 74 is rotated in the direction indicated by arrow 76 with the surface of the grinder engaging one of the surfaces, in this case, the recessed major surface of the thin region 60 of the insert. In a specific example, polishing wheel 74 comprises an ultra fine, for example, a 240 grit polishing wheel. As the wheel abrades the engaged surface of the insert, a small quantity of the insert material is removed. For example, the thickness of the thin region may be reduced by polishing from 0.0005 inch to 0.00045 inch. It has been discovered that during this abrasion process, the thin central region is drawn toward the abrading wheel as indicated in FIG. 10 and as can be seen from the gap 78 shown in this figure. Thus, the back surface of the insert in the thin region area assumes a concave configuration. During use, the concave surface may be positioned adjacent to the tooth to be treated. To the extent that the concave cavity remains during treatment, the shape of the composite resin material is affected by this concavity. Other mechanisms of achieving this concavity or bulge may be used with mechanical abrasion being the preferred approach at this time.

FIGS. 11, 12 and 13 show inserts of the respective FIG. 7, FIG. 4 and FIG. 13 forms being positioned adjacent to respective teeth to illustrate how the shape of these inserts accommodates teeth of different shapes for use in treatment of these teeth.

The thin central region of the inserts may be made by grinding, molding, casting, stamping or any other process suitable for achieving a recessed or thinned area, FIGS. 16 through 18 illustrate a chemical etching approach for use in making inserts of the form shown in FIG. 1. It being understood that inserts of the other forms shown in FIGS. 2 through 8 may be formed in the same manner. In addition, the process of FIGS. 9 and 10 may be applied to these inserts if desired.

In connection with FIG. 16, a sheet of material 80, which may be of stainless steel with a 0.015 inch thick sheet being a suitable example, is shown. A major back surface 82 of the sheet is masked with respective spaced apart bands of etch masking material, such as a photo resist material. Two such bands being indicated at 84 and 86 in FIG. 16. The bands of masking material have the overall configuration of the desired insert of FIG. 1. A water soluble photo resist such as Etertec Dry Film available from Grimes Distribution of Orange County, Calif. may be used. The opposite surface 88 of the sheet 80 is provided with a plurality of separated bands of masking material, some being indicated at 90 and 92, which are aligned with the respective bands on the opposite surface of the sheet. Thus, the band 90 is aligned with the band 84 and the band 92 is aligned with the band 86. The areas of the bands 90, 92 (indicated at 94 and 96 for band 90) which are to form the central thin regions of the insert of FIG. 1 are left unmasked. The photo resist is applied in a conventional manner, such as using a mask to shield those areas of the sheet 80 which are not to be coated with the photo resist material. The sheet containing the mask is then subjected to an acid etch, such as Ferric Chloride. As a result, the acid etches completely through the metal between the individual bands as the acid etches through the sheet 80 in these areas from both surfaces 82, 88. Thus, material such as 104 (FIG. 18) which previously joined the individual bands is removed. In addition, material 100 is removed in the thin central region of the band to the desired depth D. The masking material 84 on the surface 82 of the sheet prevents etching through, of the sheet in what is to become the central regions of the insert. Other forms of differential etching may also be used. For example, the thin central region may be etched partially from both surfaces rather than from a single surface if desired. The mask material is then stripped, for example, in a caustic soda solution. The resulting inserts may be washed and, if denied, processed to provide a concavity as described above.

While the present invention has been described in accordance with several embodiments, it is to be understood that substitutions and alterations may be made thereto without departing from the spirit and scope of the claims. I claim all such modifications which fall within the scope of the following claims.

I claim:

1. A method of producing a tooth insert for insertion between the inter proximal surfaces of at least one pair of adjacent teeth during a dental procedure, the adjacent teeth having a proximate area where the teeth are closest to or in contact with one another, the method comprising:
   providing a sheet of material with at least one central portion have a thickness of from about 0.0001 to about 0.001 inch, the central portion being at least partially surrounded by a reinforcing region of a thickness which is greater than the thickness of the central portion; and
   forming a cavity in the at least one central region.

2. A method according to claim 1 wherein the act of creating a concavity comprises polishing one surface of the at least one central region to bend material from the central region to form the concavity during polishing.

3. A method according to claim 2 in which the polishing act comprises the step of rotating a polishing wheel against said at least one central region.

4. A method according to claim 1 in which the step of providing a sheet comprises the step of providing a sheet with at least two spaced apart central portions.

5. A method according to claim 1 in which having a boundary which is the shape of a single individual tooth insert.

6. A method according to claim 1 in which the act of providing a sheet comprises providing a sheet having at least one central portion having a thickness of from 0.0003 to 0.0007 inch.

7. A method according to claim 1, in which the act of providing a sheet comprises the act of providing a sheet having a reinforcing region from about 0.001 to about 0.002 inch thick.

8. A method according to claim 7 in which the act of providing a sheet comprises the act of providing a sheet in the form of an individual tooth insert having two such spaced apart central portions which are each entirely surrounded by the reinforcing region.

9. A method according to claim 1 in which the act of forming a concavity comprises removing additional material from the thin central portion.

10. A method according to claim 1 in which the act of forming a concavity comprises removing material from the at least one central region to form a bulge in the central region.

11. A tooth insert spacer for insertion between the interproximal surfaces of a first tooth and a second adjacent tooth and between the first tooth and a third tooth at the opposite side of the first tooth from the second tooth during a dental procedure, the respective teeth having proximate areas where the teeth are closest to or in contact with one another, the tooth insert comprising:
   an elongated body having respective opposite gingival and occlusal edges and opposite side edges extending between the gingival and occlusal edges;
   the body including first and second spaced apart central portions positioned on the body such that when the body is wrapped around the first tooth, the central portions are respectfully positioned between the interproximal surfaces of the first and second teeth and the interproximal surfaces of the first and third teeth, each of the central portions having a thickness which is no more than about 0.001 inch;
   the body including a reinforcing portion which at least partially surrounds each of the central portions; and
   wherein the central portions have a thickness of from about 0.0003 to about 0.0007 inch and wherein the reinforcing position has a uniform second thickness of from about 0.015 to about 0.03 inch.

12. A tooth insert according to claim 11 in which each of the central portions is entirely surrounded by the reinforcing portion of the body.

13. A tooth spacer according to claim 11 in which the body is generally planar and wherein the central portions project outwardly in a first direction from the plane of the body.

14. A tooth insert for insertion between the interproximal surfaces of a pair of adjacent teeth during a dental procedure, the teeth having a proximate areas where the adjacent teeth are closest to or are in contact with one another, the tooth insert comprising:
   a body having a gingival edge, an occlusal edge, opposite side edges and wherein the gingival edge is arcuate;

the body also including as central portion which is at least partially surrounded by a reinforcing portion, the at least one central portion having a first thickness which is no more than about 0.001 inch, the central portion being located on the body for positioning between the inner proximal surfaces of adjacent teeth when the tooth insert is between the teeth; and wherein the central portion has a thickness which is less than the thickness of the reinforcing position.

15. A tooth spacer to claim 14 wherein the central portion is surrounded on all sides by the reinforcing portion of the body.

16. A tooth insert according to claim 14 in which the central portion extends to the gingival edge.

17. A tooth insert according to claim 14 wherein the body is generally triangular in shape with side edges which are concave and an occlusal edge which is convex.

18. A tooth insert according to claim 14 wherein the body is generally trapezoidal in shape having first and second side edges which are concave, and a gingival edge which is convex.

19. A tooth insert according to claim 14 wherein the reinforcing region surrounds the central portion and wherein the width of the reinforcing region along the gingival edge is less than the width of the reinforcing region along the occlusal edge.

* * * * *

UNITED STATES PATENT AND TRADEMARK OFFICE
CERTIFICATE OF CORRECTION

| | | |
|---|---|---|
| PATENT NO. | : 6,142,778 | |
| DATED | : November 7, 2000 | |
| INVENTOR(S) | : John. D. Summer | |

It is certified that error appears in the above-identified patent and that said Letters Patent is hereby corrected as shown below:

<u>Title page,</u>
Item [56], References Cited, the following additional references should be added:

| | | |
|---|---|---|
| 638,973 | 12/1899 | Mehlig |
| 804,099 | 11/1905 | Chase |
| 1,794,213 | 2/1931 | Spahn |
| 2,288,011 | 6/1942 | Mizzy |
| 3,074,169 | 1/1963 | Freeman |
| 3,082,531 | 3/1963 | Jacobsen |
| 3,421,222 | 1/1969 | Newman |
| 3,842,505 | 10/1974 | Eames |
| 4,373,915 | 2/1983 | Comstock |
| 4,523,909 | 6/1985 | Lazarus |
| 5,330,353 | 7/1994 | Wavrin |
| 5,505,618 | 4/1996 | Summer |

<u>Column 1,</u>
Line 46, change "class 2" to -- class 2 --

<u>Column 5,</u>
Line 23, change "direction 20 toward" to -- direction toward --

Signed and Sealed this

Twentieth Day of August, 2002

*Attest:*

*Attesting Officer*

JAMES E. ROGAN
*Director of the United States Patent and Trademark Office*